United States Patent [19]

Moorhead

[11] 4,444,787
[45] Apr. 24, 1984

[54] OPHTHALMIC TOPICAL USE OF COLLAGEN CROSS-LINKING INHIBITORS

[75] Inventor: Louise C. Moorhead, Houston, Tex.

[73] Assignee: Board of Regents, University of Texas, Austin, Tex.

[21] Appl. No.: 280,870

[22] Filed: Jul. 6, 1981

[51] Int. Cl.³ ............................................. A61K 31/275
[52] U.S. Cl. ..................................................... 424/304
[58] Field of Search .......................................... 424/304

[56] References Cited

U.S. PATENT DOCUMENTS 2,742,491   4/1958   Selilard et al. .................... 260/465.5

OTHER PUBLICATIONS

Am. Surg., 165:442 (1967)–Furlow et al.
Clin. Pharmacal. Ther., 8:593 (1967)–Keiser et al.
Ann. Surg., 178:277 (1973)–Madden et al.
Current Eye Res. 1:77 (1981)–Moorhead.
Surgery, 66:215 (1969)–Peacock et al.
J. Urol., 115:673 (1976)–Singh et al.
Wellcome Trends, Apr. –Jun. (1981)–pp. 5-6.
Chem. Abst. 77, 122,003(p) (1972)–Chansouria et al.
Chem. Abst. 78, 66682(z) (1973)–Haney et al.
Chem. Abst. 90, 66806(g) (1979)–Arem et al.
Chem. Abst. 92, 486(n) (1980)–Arem et al.

*Primary Examiner*—Douglas W. Robinson
*Attorney, Agent, or Firm*—Arnold, White & Durkee

[57] ABSTRACT

This invention relates to the treatment of wounded ocular tissue by the topical application of collagen cross-linking inhibitors to the tissue in order to reduce the cross-linking of collagen fibrils in the wounded tissue.

5 Claims, No Drawings

OPHTHALMIC TOPICAL USE OF COLLAGEN CROSS-LINKING INHIBITORS

The Government has rights in this invention pursuant to National Institutes of Health Grant No. 5K-07-EY00140.

BACKGROUND OF THE INVENTION

In all tissues of the mammalian body, there is a similar response of wounded cellular elements to injury. Injury is a process which is induced by either trauma (physical, chemical, thermal, electrical), or which results from diseases which produce acute or chronic inflammation. A fundamental phenomenon of wound healing is the metabolic activation of fibroblast cells. These cells produce the protein collagen which comprises the major portion of scar tissue.

The following brief discussion concerning the biochemistry of collagen synthesis serves to define the manner in which the wound healing response can result in permanent structural damage.

Basically, collagen molecules are synthesized within the endoplasmic reticulum of fibroblasts, stored within the Golgi apparatus, and from there are extruded into the extracellular space as procollagen. Outside of the cell, the procollagen molecules spontaneously arrange themselves by non-chemical forces into fibrils called tropocollagen. In this type of collagen, there are no chemical cross-links between individual molecules, despite a morphological appearance of mature collagen. The absence of chemical cross-linking causes the collagen to remain in an immature state. Immature collagen is characterized by a very low tensile strength, hence the scar tissue is present in usual amounts but is weak and easily pulled apart. Immature collagen is further characterized by its solubility in saline. The maturation of collagen fibrils is directly related to the formation of cross-links between individual collagen molecules.

The cross-linking of collagen molecules is controlled by the enzyme lysyl oxidase. The cross-linking occurs in two stages with the first stage involving the enzymatic synthesis of aldehydes in the presence of lysyl oxidase. This stage is shown by the following chemical reaction:

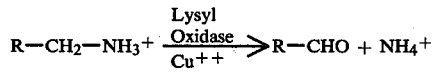

The reaction involves the removal of terminal amino groups from lysyl or hydroxylysyl residues in the tropocollagen. The copper-containing enzyme lysyl oxidase serves as the catalyst. After the first stage is complete and the aldehydes are produced, one of the two following cross-linking reactions may occur:

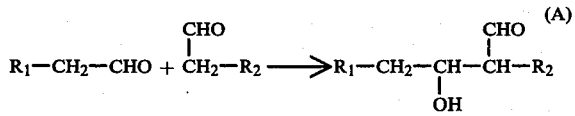

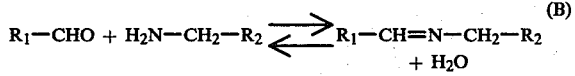

Reaction A produces a stable and irreversible intermolecular bond, with no further reactions necessary.

Reaction B involves the reversible production of a Schiff base, which is subsequently reduced to produce a stable cross-link. Both of the cross-linking reactions involve intermolecular bonding which significantly increases the tensile strength of collagen and thereby results in a mature collagen fiber.

It is known that the cross-linking of collagen fibrils can be prevented by the use of agents which have their effect either by inhibiting the enzyme, lysyl oxidase, or by binding to the aldehydes produced as a result of its action. Beta-aminopropionitrile (BAPN), aminoacetonitrile, beta-mercaptoethylamine, dithiothreitol, isoniazide, iproniazide, carbonyl reagents, disulfhydryls and diamines are all known to cause in vitro inhibition of lysyl oxidase.

D-pencillamine is known to have two effects on the collagen cross-linking process: to reversibly inhibit the lysyl oxidase; and to irreversibly bind to the aldehydes generated as a result of its action. BAPN and d-pencillamine apparently have the best in vivo effects of the above mentioned agents, and, therefore, have been the most closely investigated.

BAPN was first isolated from sweet peas, or *Lathyrus odoratus*. Interestingly, it was farmers whose cattle grazed on sweet peas who noted that their cattle developed bone and joint abnormalities and that some died from ruptured aortic aneurysms. It was discovered that this condition, now known as lathyrism, resulted from BAPN's inhibition of lysyl oxidase.

The inhibition of lysyl oxidase has been disclosed in the literature. Page and Benditt postulated that the mechanism of BAPN-induced lathyrism is due to its irreversible inhibition of lysyl oxidase in 1967 in Biochemistry, Vol. 6, pages 1142–1147 and in the Proceedings of the Society for Experimental Biology and Medicine, Vol. 124, pages 454–459.

BAPN has been used systemically in humans to control the tensile strength of fibrous tissue involved in scleroderma, flexor tendon repair, and urethral stricture. Keiser and Sjoerdsma attempted to treat humans afflicted wich scleroderma with orally-administered BAPN and disclosed their results in Clinical Pharmacology and Therapeutics, Vol. 8, No. 4, pps. 593–602. Four patients were treated for 22 to 67 days. A reversible periosteal reaction occurred in one patient and untoward effects were observed in patients at a dose level which produced only moderate effects on skin collagen and no apparent therapeutic effect. The authors proposed that future use of the drug as an inhibitor of collagen cross-linking in man should be limited to short term trials.

In a report entitled, "Some studies on the effects of Beta-aminopropionitrile in patients with injured flexor tendons," published in 1969 in Surgery, Vol. 66, pps. 215–223, Peacock and Madden disclosed that they orally administered BAPN to humans following repair of flexor tendons but discontinued the study because of undesirable systemic reaction. Another publication by Peacock et al. entitled, "Administration of Beta-aminopropionitrile to Human Beings with Urethreal Strictures: A Preliminary Report," published in November, 1978, Vol. 136 issue of the American Journal of Surgery, reported the reduction in breaking strength of newly formed connective tissue in patients systemically treated with very low doses of BAPN. The patients did not develop signs of toxicity; however, the clinical proof of their improvement as a result of the BAPN systematic treatment was equivocal.

Apparently, the many side effects associated with the systemic use of BAPN have prevented the widespread acceptance of the inhibitor by the medical profession. A February 1972 article entitled, "Caution Against the Use of Lathyrogens," by Barrow et al. appearing on pages 309–310 in Vol. 71, No. 2 of Surgery, discloses BAPN's function as a lathyrogenic agent but urges great caution in the use of such agents.

Other publications have disclosed the effects of other compositions known to inhibit collagen fibril cross-linking. One such disclosure is made in ARVO abstracts, 1980 by Brancato et al. in which it is reported that the oral administration of d-penicillamine to rabbits for 14 days resulted in an increase in the solubility of vitreous collagen. No clinical proof of the efficacy of oral administration of d-penicillamine was reported. A 1976 publication entitled, "Lathyritic Activity of Isoniazid," appearing in Vol. 7, Nos. 3 and 4 of the Journal of Medicine suggests that the therapeutic effectiveness of isoniazide as an antituberculous drug might reside in its lathyritic activity.

One of the difficulties with compositions which are utilized to inhibit collagen cross-linking is that some of the composition may be metabolized before its lathyritic action is initiated or completed. It is desirable to limit the metabolism of collagen cross-linking inhibitors under certain circumstances. A 1979 article entitled, "Effect of Pargylene on the Metabolism of BAPN by Rabbits," Toxicology and Applied Pharmacology 47, pps. 61–69 discloses the reduction of BAPN degradation by the monoamine oxidase inhibitor pargylene and suggests that the chemical might be useful in prolonging the biological activity of BAPN.

Although the literature discloses the systemic use of collagen cross-linking inhibitors in the treatment of either trauma-induced or disease-induced wounds, it would appear that such a use has not received widespread medical acceptance.

Scarring in tissue located anywhere in the body may cause permanent alterations in the usual anatomical structures of the wounded tissue. Nowhere are complications from scarring more pronounced than in ocular tissue. Contracting collagen fibers produce traction which can cause very undesirable conditions in ocular tissue. After trauma to the external ocular structures, for example, undesirable effects may result from malrotation of the lids, trichiasis, and fornix contracture. Diseases which are external to the eyeballs can also cause difficulties. In cicatricial inflammatory diseases such as pemphigoid and Stevens-Johnson syndrome, the fornix of the eye may shrink and be completely obliterated.

There are other situations in which contraction caused by the maturation of collagen in healing ocular wounds can result in undesirable effects. In the surgical procedure to correct near-sightedness, radial keratotomy, the cornea is subjected to numerous deeply penetrating incisions. The results of this surgery are quite variable It is likely that the unpredictability of the surgical results is associated with the contraction of collagen fibers during the healing of the incisions.

The problems attendant to cataract surgery present another area in which contracting collagen fibers can cause difficulties. Anterior chamber intraocular lenses may be dislocated by contracting peripheral anterior senechiae and the pupil may be distorted as a result of scarring.

There are still other difficulties which scarring of ocular tissue poses to the patient as well as the ophthalmologist. Retinal traction and sometimes detachment may be caused by vitreous collagen contraction and shrinking. Surgical procedures utilized in the treatment of glaucoma many times are unsuccessful. For example, the failure of glaucoma filtering procedures may be caused by the contraction and tightening of cicatricial collagenous bands stretching across the fistula.

Most of the difficulties which the ophthalmologist faces by virtue of contracting collagen fibers have been dealt with surgically. It would be desirable to reduce or completely eliminate the undesirable effects caused by the contraction of maturing collagen fibers located in ocular tissue by the employment of a safe, relatively inexpensive and expedient method.

SUMMARY OF THE DISCLOSURE

The undesirable effects of the shrinkage and contracture of collagen fibrils located in ocular tissue may be significantly reduced or completely eliminated by the topical application of an effective amount of a pharmacologically suitable composition containing one or more collagen cross-linking inhibitors. The composition may be applied either directly to the collagen fibrils sought to be prevented from cross-linking or the composition may be applied to tissue relatively close to the collagen fibrils sought to be affected such that the cross-linking of the fibrils is significantly reduced or completely eliminated. The composition should be applied to the tissue for a period of time not less than the time required for the stabilization of the acute wound healing of the tissue sought to be affected.

The method of the instant invention involves the treatment of wounded mammalian ocular tissue with a pharmacologically suitable composition containing a collagen cross-linking inhibitor effective to reduce the cross-linking of collagen fibrils in the wounded tissue. Wounded ocular tissue refers to tissue which has been injured by trauma or as a result of any disease which produces acute or chronic inflammation. The ocular tissue which may be treated in accordance with the method of this invention includes those structures within the globe of the eye, its external surface, and those closely adjacent to it which are essential for the structure and function of the mammalian eye and visual system. This tissue includes the conjunctiva and adjacent lid structures, the lacrimal system, the sclera, cornea, angle structures, iris, lens, ciliary body, vitreous, retina, choroid, optic nerve, and all associated nerve and vascular structures. The skin beyond the orbital area is excluded from the definition of ocular tissue.

Throughout this disclosure the term "stabilization of the acute wound healing process" or words of similar import are intended to mean the end phase of the wound healing process in which fibroblasts are no longer metabolically active and manufacturing collagen and in which evidence of lysyl oxidase activity is minimal. The term "collagen cross-linking inhibitor" or words of similar import has reference to those compounds known as lathyrogens which limit the production of aldehydes involved in the collagen cross-linking process and to any other compound which prevents or substantially reduces the collagen cross-linking process, irrespective of the mechanism involved.

Generally, the inhibitors which may be utilized in the practice of this invention include any chemical capable of preventing the cross-linking of collagen fibrils and which does not otherwise destroy or adversely affect ocular tissue not intended to be affected by the treatment of this invention. The specific inhibitors which may be utilized in the method of this invention consist essentially of BAPN in either the free base or fumarate salt form, aminoacetonitrile, beta-mercaptoethylamine, dithiothreitol, isoniazide, iproniazide, disulfhydryls, diamines, and penicillamine. Although no testing of the efficacy of carbonyl reagents has been undertaken, it is believed that this type of inhibitor could also be utilized. These inhibitors may be utilized alone or in combination of each other.

The pharmacologically suitable composition containing the inhibitor may be formulated in solution form or in the form of an ointment. Although any pharmacologically suitable carrier may be used, an ointment is preferred since it should stay in place more easily on the tissue to which it has been topically applied.

When the wounded ocular tissue requiring treatment is identified, the pharmacologically suitable composition containing the lathyrogen is applied to the tissue over a period of time not less than that required for the stabilization of the acute wound healing of the tissue to be treated. It is anticipated that the application of the composition three times a day for a minimum of three weeks should be effective in reducing the cross linking of collagen fibrils in the wounded tissue.

DETAILED DESCRIPTION OF THE PREFERRED EMBODIMENT

The pharmacologically suitable composition which may be employed in the treatment of this invention comprises a carrier and a collagen cross-linking inhibitor. The carrier may be any solution or ointment which does not adversely affect ocular tissue and which does not alter the chemical efficacy of the inhibitor such that the reduction of cross-linking of collagen fibrils is adversely affected.

Although an ointment carrier is preferred since it will stay in place on the tissue to which it is applied, other carriers such as a physiologically stable buffered saline solutions may be utilized. The saline solution should have a pH of about 7.4. The ointment which may be utilized as a carrier may be generally characterized as a bland ointment and specifically is of a type similar to Lacrilube produced by Allergan.

The concentration of inhibitor contained in the pharmacologically suitable composition may range from about 25 percent to about 50 percent by weight of the composition. Although compositions having weight concentrations of inhibitors greater that 50% may be utilized, they are not preferred since their use would likely irritate the tissue to be treated and be of some discomfort to the patient. Compositions having less than 25 percent by weight of inhibitor may be utilized but are not preferred since it is believed that the frequency of treatment would be increased. Preferably the concentration of inhibitor should be no greater than 50% by weight of the composition, with 33 percent by weight being the most preferred concentration.

The preferred inhibitor for use in accordance with the treatment of this invention is BAPN fumarate. The free base form of BAPN may be utilized but it is not preferred. The preferred pharmacologically suitable composition of the instant invention comprises a combination of BAPN fumarate and a bland ointment such as Lacrilube in a weight ratio of 1 part BAPN to 3 parts ointment.

In preparing the preferred composition, the BAPN fumarate is ground to a fine powder by use of a mortar and pestle. Three grams of the ointment is slowly heated on a hot plate to liquify the ointment. Then, one gram of the powdered BAPN is admixed with the liquified ointment. The admixture is poured into jars and allowed to cool at room temperature.

This procedre does not provide for sterilization of the admixture; however, it should be apparent that any suitable technique may be utilized.

In the treatment of this invention, once the wounded ocular tissue to be treated is identified, the composition containing the inhibitor is topically applied directly to the tissue sought to be treated. In the case of a liquid composition, eye drops can be placed on the tissue directly from an eyedropper. When using an ointment carrier, the composition can be applied to the tissue directly from the tube containing the ointment. In the treatment of some wounded ocular tissue such as the vitreous which is not normally exposed and therefore susceptible of direct topical treatment the composition containing the inhibitor can be applied to the cornea and it should infuse through the anterior chamber around the lens and into the vitreous body.

Although there is no precise number of applications or dosages to be applied to the wounded tissue in accordance with this invention, it is preferred to apply the composition containing the inhibitor three times daily for a total period of time not less than the time required for stabilization of the acute wound healing process. In general, it is preferred that the application three times a day be maintained for no less than three weeks.

In the treatment of a human having wounded ocular tissue, it is preferred to keep the eye covered for the duration of the treatment in order to reduce unwanted removal of the treatment ointment. The eye, however, need not be covered.

The following experiments conducted on rabbits are exemplary. These experiments confirm the feasibility of using collagen cross-linking inhibitors in ocular tissue The data collected in the experiments verifies that BAPN and d-penicillamine both limit the degree of scarring in clinical animal models.

EXPERIMENT 1

This experiment was run to obtain a determination of the effect of BAPN on conjunctival scaring.

MATERIALS AND METHODS

In this experiment injury was produced in sedated and anesthethized adult pigmented rabbits by placing a moistened sodium hydroxide pellet in the inferior fornix and moving it about the conjunctiva for 30 seconds. Immediately following removal of the pellet, the eyes were irrigated with distilled water for 2 minutes. A large scleral shell was utilized to protect the cornea during the injury inducement procedure.

The right eye of all animals received the induced alkali injury to the conjunctiva while the left eye was not injured.

The composition containing BAPN was produced by mixing one part by weight of BAPN fumarate (Catalogue No. A7,642-7 available from Aldrich) with 3 parts by weight of a bland ointment base sold under the trademark Lacrilube by Allergan. Before admixture the BAPN was ground to a fine powder and the ointment was slowly heated until liquified.

The animals involved in the treatment were divided into two groups: those whose eyes received the topical application of the composition containing BAPN and those receiving only the ointment base without any added BAPN. Both eyes of eleven rabbits were treated with the BAPN ointment while both eyes of nine rabbits were treated with the ointment base without any added BAPN. Hence, four separate groups of eyes were involved in the experiment:

(1) Scarred eyes which were treated with the BAPN ointment composition "N=11";
(2) Scarred eyes to which the ointment base not having BAPN was applied "N=9";
(3) Unscarred eyes which were treated with the BAPN ointment "N=11"; and
(4) Unscarred eyes to which the ointment base not having BAPN were applied "N=9"

The ointment either with or without BAPN was topically applied to all eyes three times a day for 21 days after the day on which the inuries were induced. A total of approximately 3 milligrams of ointment was applied to the eyes during each separate treatment. During the treatment, all eyes were treated once daily with gentamycin sulfate (Garamycin from Schering) eyedrops for antibiotic prophylaxis. The animals were treated by a third party to remove bias of the investigator.

On the 21st day after injury inducement, the animals were randomly coded by the 3rd party and both eyes were clinically examined by slit lamp biomicroscopy, applanation tonometry and dilated fundoscopy. The following day randomly coded animals were sacrificed and the length and width of the interpalpebral fissure of all eyes were measured with ophthalmic calipers. Subconjunctival tissue was then harvested from all eyes for morphological analysis.

RESULTS

The mean interpalpebral fissure measurements of both the length and width appear in Tables 1 and 2. In the injured eyes, comparison of the control values with the treated yielded a significant p value of less than 0.025. Comparison of the control uninjured eyes with the treated uninjured eyes revealed p value of less than 0.200. These results verified that BAPN caused no significant change in the interpalpebral fissure measurements of uninjured eyes. Further statistical analysis was performed with the percent difference of the length and width:

$$\text{length \% difference} = \frac{LL - LR}{LL} \times 100;$$

$$\text{width \% difference} = \frac{WL - WR}{WL} \times 100$$

(LL=length of left eye, LR=length of right eye, WL=width of left eye, WR=width of right eye.) The significance of the measurements, especially the percent difference in interpalpebral fissure width, is shown in Table 3.

Morphological studies including inspection of the control conjunctival epithelium and the subconjunctival cicatricial tissue was undertaken. The studies reveal that the control tissue is filled with collagen, and the fibroblasts appear compact with deeply basophilic nuclei. In the BAPN-treated tissue, there were areas in which the fibroblasts were more abundant, more irregular in shape, and larger than in control tissue. In addition, the fibroblast nuclei appeared somewhat less basophilic and the cytoplasm more basophilic than the controls. These changes have been shown to be characteristic of lathyritic tissue.

The collagen fibrils from the control group which developed as a response to alkali injury were also studied using electron microscopy. Induction of localized lathyrism by the topical application of BAPN caused no disruption of the basic architecture of the collagen. However, the mean fibril width of collagen from injured tissue treated with BAPN was almost 100 angstroms larger than the control collagen fibrils. This difference might be explained by the failure of each collagen fibril to pack tightly because of the decreased intermolecular cross-linking produced by BAPN. Ultrastructural examination of the cellular elements in the treated tissue did not reveal signs of toxicity from BAPN.

As part of the experiment the possible side effects of the topical application of BAPN were evaluated.

Observation of the BAPN-treated and control animals during the treatment period did not demonstrate any obvious differences in behavior or feeding habits. On the day before sacrifice, all animals were examined clinically by slit lamp biomicroscopy, applanation tonometry, and dilated fundoscopy. Because of fornix contracture and some corneal scarring, IOP measurements and fundus examinations were not performed in all the injured eyes. However, all uninjured eyes from both treatment groups were evaluated, and no differences in the appearance of the anterior and posterior segments or intraocular pressure were observed.

TABLE 1

| | Fissure length (mm) | | |
|---|---|---|---|
| | BAPN* | Control** | Value |
| Injured eyes | 11.6 ± 0.3 | 10.1 ± 0.6 | <.025 |
| Uninjured Eyes | 15.0 ± 0.1 | 14.7 ± 0.3 | <.200 |

*Mean ± SEM; N = 11
**Mean ± SEM; N = 9

TABLE 2

| | Fissure Width (mm) | | |
|---|---|---|---|
| | BAPN* | Control** | Value |
| Injured Eyes | 7.0 ± 0.4 | 5.5 ± 0.5 | <.025 |
| Uninjured Eyes | 8.9 ± 0.2 | 8.2 ± 0.4 | <.200 |

*Mean ± SEM; N = 11
**Mean ± SEM: N = 9

TABLE 3

Kruskal-Wallis Analysis of Percent Difference of Interpalpebral Fissure

| | Length | Width |
|---|---|---|
| Control Mean Rank | 13.17 | 13.78 |
| BAPN mean rank | 8.32 | 7.82 |
| $X^2$ corrected for ties | 3.375 | 5.131 |
| p | .066 | .024 |

TABLE 4

| COLLAGEN FIBRIL WIDTH - INJURED EYES | | |
|---|---|---|
| | Mean ± SEM (Angstrom) | p Value |
| Control* | 708 ± 7.5 | |
| BAPN** | 805 ± 9.5 | <.001 |

*3 different eyes; 140 measurements
**4 different eyes; 140 measurements

EXPERIMENT 2

This experiment was conducted in order to determine the effect of BAPN and D-penicillamine on conjunctival scarring. In this experiment pigmented rabbits were sedated and anesthesized and conjunctival injury was induced in the right eye as described in experiment 1. The left eye of all animals was not injured. In this experiment a bland ointment as described in experiment 1 was utilized and a BAPN inhibitor ointment as described in experiment 1 was utilized. Also, an inhibitor ointment made of D-penicillamine was made using the same ratio of inhibitor to ointment as described in experiment 1 with respect to the BAPN ointment. The 1:3 BAPN ointment and 1:3 D-penicillamine ointment were mixed together in equal weights to produce an ointment having both BAPN and D-penicillamine.

In this experiment, both eyes of five animals were treated with the bland ointment, both eyes of six animals were treated with the D-penicillamine ointment, both eyes of six animals were treated with the BAPN ointment, and both eyes of five animals were treated with the BAPN/D-penicillamine combination ointment. The same treatment method described in experiment 1 was utilized in this experiment. On the 21st day, however, the animals were randomly coded, sacrificed, and only the interpalpebral fissures were measured as in experiment 1.

The statistical analysis of the measurements verified that both the BAPN ointment and a combination of the BAPN/D-penicillamine ointment caused a significant reduction of collagen cross linking. The percent differences of the various groups are listed in Table 5. The P values are listed in Table 6 and the Mann-Whitney-Wilcoxon Rank Sum Test is listed in Table 7.

TABLE 5

Percent Difference of Interpalpebral Fissure between Left and Right Eye

|  | Length | Width |
| --- | --- | --- |
| Control | 25.25 ± 1.79* | 11.94 ± 3.53 |
| Penicillamine | 20.20 ± 3.76 | 9.54 ± 4.74 |
| BAPN | 8.48 ± 6.26 | −9.58 ± 13.24 |
| Combination | 15.38 ± 2.32 | −.500 ± 3.571 |

*Standard error of the mean.

TABLE 6 p-values of the percent difference

|  | Control vs. | p-value |
| --- | --- | --- |
| Length | Penicillamine | .264 |
|  | BAPN | .042 |
|  | Combination | .010 |
| Width | Penicillamine | .693 |
|  | BAPN | .167 |
|  | Combination | .038 |

TABLE 7

Mann-Whitney Wilcoxon Rank Sum Test

|  | Control vs. | p |
| --- | --- | --- |
| Length | Penicillamine | .0957 |
|  | BAPN | .0525 |
|  | Combination | .0259 |
| Width | Penicillamine | .5704 |
|  | BAPN | .0555 |
|  | Combination | .0290 |

While the preferred embodiment of this invention should be understood to be the best mode presently contemplated, it should also be understood that it is not the only embodiment possible. The scope of this invention, hence, shall be defined by the following claims and by any equivalent modification and variations which may fall within the true spirit and scope of the invention.

What is claimed is:

1. A method for treating wounded mammalian ocular tissue to reduce the cross-linking of collagen fibrils in said tissue, comprising: the topical application of a pharmacologically suitable composition comprising an admixture of a therapeutically effective amount of BAPN with a suitable topical vehicle.

2. The method of claim 1 wherein the concentration of BAPN ranges from about 25 to about 50 percent by weight of said composition.

3. The method of claim 2 wherein said composition comprises BAPN admixed with a physiologically stable buffered saline solution.

4. The method of claim 1 wherein said pharmacologically suitable composition comprises BAPN admixed with a suitable ointment.

5. The method of claim 1 wherein said pharmacologically suitable composition comprises BAPN admixed with a suitable ointment and the concentration by weight of BAPN is not greater than 50% of said composition.

* * * * *